United States Patent [19]
Hijikata

[11] 3,932,132
[45] Jan. 13, 1976

[54] SYSTEM FOR DETECTING THE PARTICULAR CHEMICAL CONSTITUENT OF A FLUID

[75] Inventor: Kazuo Hijikata, Hachioji, Japan

[73] Assignee: Olympus Optical Co., Ltd., Tokyo, Japan

[22] Filed: July 23, 1974

[21] Appl. No.: 490,984

[30] Foreign Application Priority Data
July 31, 1973 Japan.............. 48-86168
July 31, 1973 Japan.............. 48-86169
July 31, 1973 Japan.............. 48-86171
July 31, 1973 Japan.............. 48-86172

[52] U.S. Cl........ 23/253 R; 23/253 TP; 235/151.35
[51] Int. Cl.$^2$.................. G01N 33/16; G01N 21/30
[58] Field of Search............ 23/253 R, 253 TP, 259, 23/230 R; 235/151.35

[56] References Cited
UNITED STATES PATENTS

| | | | |
|---|---|---|---|
| 3,497,320 | 2/1970 | Blackburn et al. | 23/253 X |
| 3,526,480 | 9/1970 | Findl et al. | 23/253 TP |
| 3,535,084 | 10/1970 | Izawa et al. | 23/253 R |
| 3,554,700 | 1/1971 | Maxon | 23/253 X |
| 3,728,080 | 4/1973 | Moran | 23/253 X |
| 3,770,382 | 11/1973 | Carter et al. | 23/253 R |

Primary Examiner—R. E. Serwin
Attorney, Agent, or Firm—Flynn & Frishauf

[57] ABSTRACT

A system for detecting the particular chemical constituent of a fluid which comprises a photoelectric conversion device for giving forth an electric signal having an amplitude exactly corresponding to the changed color of an absorptive carrier containing a reagent which results from a chemical reaction between a test fluid and the reagent contained in said carrier; a calibration device for eliminating unnecessary components from said electric signal; a device for comparing an output signal from the calibration device with referential data having preset values to determine the sequential position which the measured degree of chemical reaction between the reagent and the test fluid occupies among the various values of said referential data; a printing device for printing out an output from said comparing device representing the content of the desired chemical constitutent of the test fluid.

5 Claims, 12 Drawing Figures

SYSTEM FOR DETECTING THE PARTICULAR CHEMICAL CONSTITUENT OF A FLUID

This invention relates to a system for detecting the particular chemical constituent of a fluid which consists in measuring the degree of chemical reaction between a reagent contained in an absorptive reagent carrier and a test fluid by an output electric signal from a photoelectric conversion device which exactly corresponds to an optical change in the reagent carrier.

Figure 1:
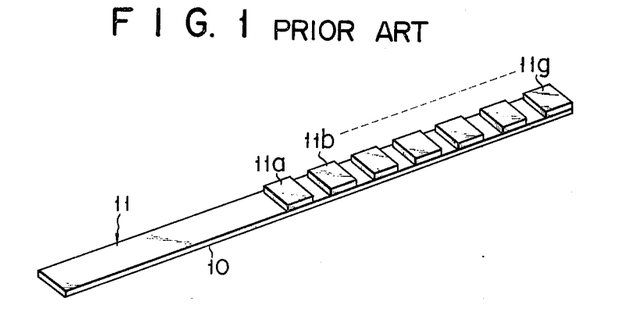
FIG. 1 is an oblique view of a prior art chemical reaction testing piece.

The known chemical reaction-testing piece is formed, as shown in FIG. 1, of a plurality of carriers 11a to 11g coated or impregnated with different kinds of chemical reagents and spatially bonded on a narrow transparent substrate 11. This testing piece is generally used in examining a test fluid, for example, urine. The prior art examination of a test fluid using said testing piece has been effected by immersing the testing piece in the test fluid or dripping the test fluid on the respective reagent carriers to impregnate them with the test fluid and continuing a chemical reaction between the test fluid and the various reagents for a prescribed length of time. Since the reagents, namely, the reagent carriers present different colors according to the various degrees of chemical reactions, comparison is made between the changed colors of the respective reagent carriers and those given in a colorimetric chart to examine what degrees of chemical reactions are represented by the changed colors, namely the sequential positions of the respective degrees of chamical reaction thereby determining the physical properties of the test fluid, such as the pH value of the whole fluid and the concentration of a particular constituent thereof.

The customary test using the above-mentioned chemical reaction-testing piece has the drawback that since the colors of the respective reagent carriers are determined by naked eye with reference to the colorimetric chart, the test is accompanied with the possibility of test results being affected by the mental differences of individuals engaged in the test. Therefore, strong demand has been made for the development of a system capable of more accurately determining the degrees of chemical reactions between the test fluid and the reagents of carriers, namely, the colors appearing thereon as the result of said reactions.

SUMMARY OF THE INVENTION

It is accordingly the object of this invention to provide a system for detecting the particular chemical constituent of a fluid which always gives accurate test results. This object is attained by a system according to this invention wherein a photoelectric conversion device gives forth an electric signal representing a degree of chemical reaction between a test liquid and a reagent contained in a carrier, namely, the changed color of the reagent carrier; and the electric signal is calibrated, if required, to eliminate unnecessary components therefrom, thereby attaining the accurate determination of the degree of said chemical reaction.

BRIEF DESCRIPTION OF THE DRAWINGS

This invention can be more fully understood from the following detailed description when taken in conjunction with the accompanying drawings, in which.

DETAILED DESCRIPTION OF ILLUSTRATED EMBODIMENTS

Figure 2:
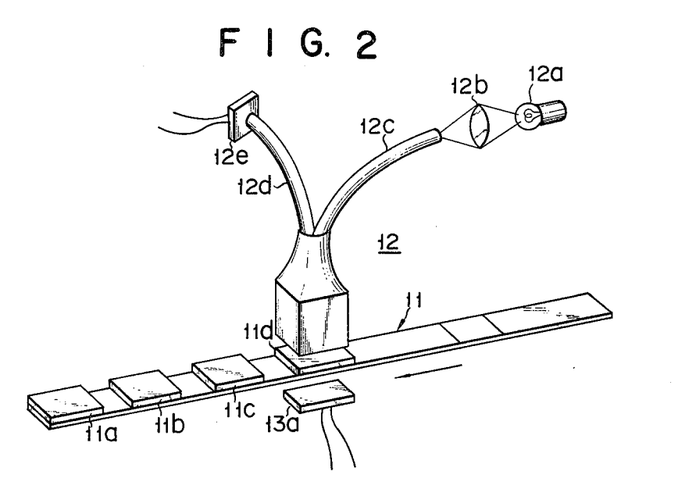
FIG. 2 is an oblique view of the electric signal-detecting section of the chemical constituent-detecting system of this invention.

Referring to FIG. 2, a chemical reaction testing piece 11 used in this invention comprises of a plurality of absorptive reagent carriers 11a to 11g containing different reagents and spatially bonded on a transparent substrate 10. The testing piece 11 is shifted each time for a distance equal to the pitch between the respective reagent carriers 11a to 11g. A photoelectric conversion device 12 is always positioned on each reagent carrier so as to determine the degree of a chemical reaction between a test fluid and the reagent contained in each reagent carrier. Provided near the underside of the testing piece 11 is a photoelectric element 13a included in a device for distinguishing the type of testing piece used (represented by a code detector shown in FIG. 3). The photoelectric conversion device 12 projects the light generated by a lamp 12a on the surface of, for example, the reagent carrier 11d through a focusing lens 12b and light guide 12c, and conducts a light reflected from said surface to another photoelectric element 12e through another light guide 12d for photoelectric conversion. When testing piece 11 passes over the photoelectric element 13a prior to the measurement by the photoelectric conversion device 12 of the degrees of chemical reactions between a test fluid and the reagents contained in the respective reagent carriers 11a to 11g, the testing piece type-distinguishing device 13 receives a light passing through the transparent substrate 10 to detect a code representing the arrangement of said reagent carriers 11a to 11g on the substrate 10. Now, let it be assumed that when shut off from light passing through the transparent substrate 10, the photoelectric conversion device 12 generates an output of 0 and, when exposed to light passing through said photoelectric conversion device 12, gives forth an output of 1. Further where, in the case of FIG. 2, the testing piece 11 is supposed to move in the direction of the indicated arrow, then the photoelectric element 13a produces a coded output of 0101010 for the reagent carrier 11d, and a coded output of 010 for the reagent carrier 11b. A device 13 for distinguishing the type of testing piece 11 detects coded signals denoting the reagent carriers 11a to 11g arranged on the substrate 10 as shown in FIG. 2, namely, the kinds of reagents contained in said carriers 11a to 11g thus arranged, that is, the type of testing piece 11 formed of these carriers.

Figure 3:
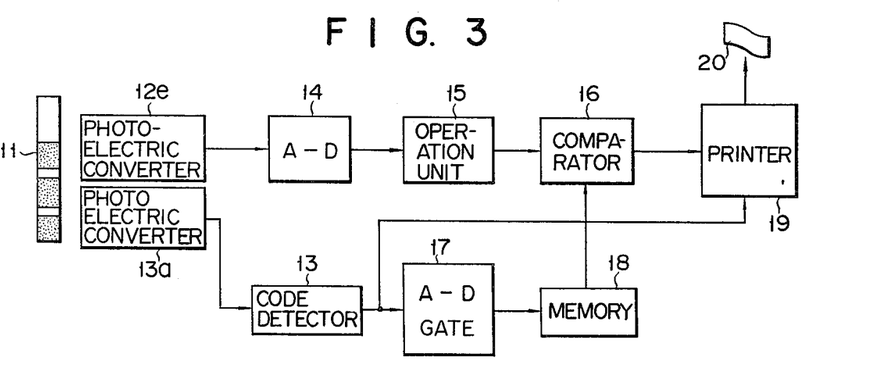
FIG. 3 is a block circuit diagram of the detecting system of the invention.

On the other hand, a light projected on, for example, the reagent carrier 11d from the lamp 12a through the light guide 12c is reflected according to the kind of color appearing on the reagent carrier 11d which corresponds to a degree of chemical reaction between a test fluid and the reagent contained in said carrier 11d. The reflected light is converted to an analog signal by the photoelectric element 12e and conducted to an analog-digital converter 14, where the signal is changed into a digital signal having a frequency (or a number of pulses) corresponding to the amplitude of said analog signal. A digital output from the A-D converter 14 is calibrated in an arithmetic operation circuit 15 and produced as a signal denoting the measured degree of a chemical reaction between the test fluid and the reagent contained in the carrier 11d. Said signal is conducted to a comparator 16.

Figure 4:
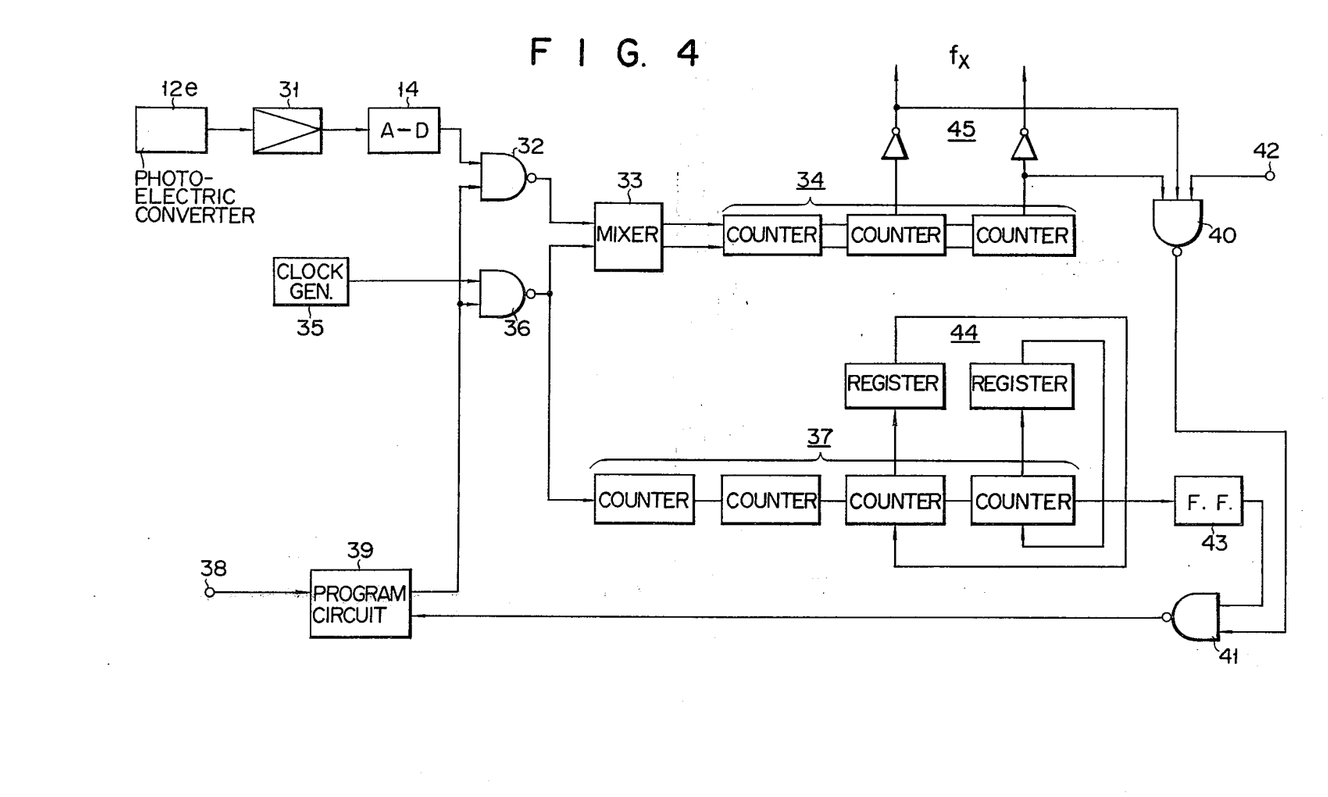
FIG. 4 is a concrete block circuit diagram showing the analog-digital conversion circuit of FIG. 3 and a calibration circuit included in the arithmetic operation circuit of FIG. 3.
Figure 5:
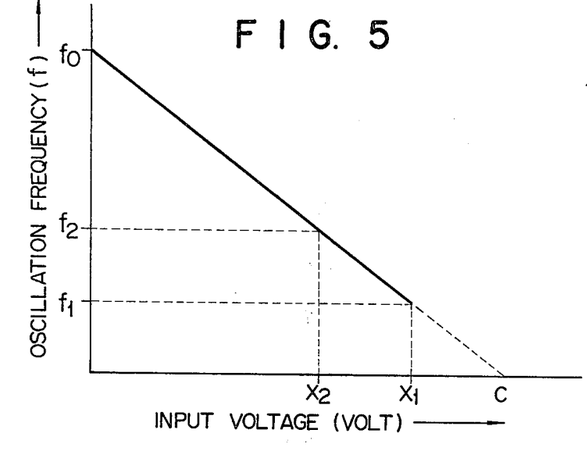
FIG. 5 is a graph showing the relationship of an input to and an output from the A-D conversion circuit of FIG. 4.

FIG. 4 concretely shows the A-D converter 14 and the calibration circuit included in the arithmetic operation circuit 15. An output analog signal from the photoelectric element 12e is amplified by an amplifier 31 and conducted to the A-D converter 14 consisting of a voltage-frequency conversion oscillator, namely, a voltage controlled oscillator having input voltage-frequency characteristics as illustrated in FIG. 5. This A-D converter or oscillator 14 makes oscillations at a maximum frequency $f0$ when the input voltage is zero volt and has its oscillation frequency linearly decreased in inverse proportion to increasing input voltage, and, when the input voltage reaches C volts, has its oscillation stopped. Actually, however, the oscillator 14 presents a frequency $f1$ or a minimum frequency when input voltage is X1 volts and, when the input voltage further decreases, has its oscillation stopped.

When, therefore, input voltage stands at X volts, the frequency $fx$ of the above-mentioned oscillator 14 may be expressed as $$fx = -\frac{f0}{C} \cdot X + f0 \quad (1)$$

Accordingly, when used in detecting the particular chemical constituent of a referential sample of fluid, the oscillator 14 makes oscillations at a frequency $f1$ expressed as follows:

$$f1 = -\frac{f0}{C} \cdot X1 + f0 \quad (2)$$

When the oscillator 14 continues oscillations at a frequency $f1$ for a time $t1$, then pulses will be generated in the following number $P1$:

$$P1 = f1 \cdot t1 = f0 \cdot t1 \left(-\frac{X1}{C} + 1\right) \quad (3)$$

The above equation (3) represents the case where it is supposed that a light projected on the referential sample of fluid does not change in luminosity, and drift current does not occur in the photoelectric element 12e. In practice, however, the detecting system is used for long hours, giving rise to the decreased luminosity of a light projected on samples of fluid, the occurrence of drift current in the photoelectric element 12e and changes in the level of an analog signal as well as in the frequency $f1$ of the oscillator 14.

Where, therefore, it is assumed that an analog signal supplied to the oscillator 14 has its level reduced to $1/n$ of X1, namely, X2, then the oscillator 14 will make oscillations at a frequency $f2$ expressed as follows:

$$f2 = -\frac{f0}{C} \cdot X2 + f0 = -\frac{f0}{C} \cdot \frac{X1}{n} + f0 \quad (4)$$

At this time, the oscillator 14 produces pulses in the following number $P2'$:

$$P2' = f2 \cdot t1 = f0 \cdot t1 \left(-\frac{X1}{C} \cdot \frac{1}{n} + 1\right) \quad (5)$$

Thus the pulse number $P2'$ is different from the first mentioned pulse number $P1$.

Now let it be assumed that the time of measurement at an oscillation frequency $f2$ is changed to $n$ times $t1$, namely, to $t2$, then pulses will be given forth in the following number $P2$:

$$P2 = f2 \cdot t2 = f2 \cdot nt1 = f0 \cdot nt1 \left(-\frac{X1}{C} \cdot \frac{1}{n} + 1\right)$$

$$= f0 \cdot t1 \left(-\frac{X1}{C} + n\right) \quad (6)$$

Therefore, $$P1 - P2 = f0 \cdot t1 \left(-\frac{X1}{C} + 1\right) - f0 \cdot t1 \left(-\frac{X1}{C} + n\right)$$

$$= f0 \cdot t1 (1 - n) \quad (7)$$

Thus the pulse number $P1$ may be expressed as follows:
$$P1 = f0 \cdot t1(1-n) + f2 \cdot nt1 = nt1(f2 - f0) + f0 \cdot t1 \quad (8)$$

If, therefore, there is provided a circuit capable of carrying out the arithmetic operation of the above equation (8) to determine the value of $nt1$ from said circuit, measurement is made on a given fluid sample, whose particular chemical constituent is unknown by continuing reaction between said fluid and the reagents for a time $nt1$, and the number of pulses generated during said measurement is counted, then it will be possible to produce prescribed numbers of pulses with respect to the respective reagents contained in the carriers, regardless of whether a light projected on said sample decreases in luminosity or whether drift current appears in the photoelectric element 12e with the resultant change in the frequency of the oscillator 14, thereby attaining the accuracy of said measurment.

Referring to FIG. 4, an output from the oscillator 14 is supplied to the up-counting input terminal of an up-down counter 34 through a NAND gate 32 and pulse mixer 33 to cause said counter 34 to carry out up-counting. Further, a referential signal generator 35 is provided to deliver referential pulses of a prescribed frequency to the down-counting input terminal of the up-down counter 34 through a NAND gate 36 and pulse mixer 33 to cause said counter to carry out down-counting. The referential pulses are also conducted to the elements of the timer counter 37 successively through a NAND gate 36 to be counted thereby. A program circuit 39 operated upon receipt of a measurement-instructing signal from an input terminal 38 supplies a gating signal to the NAND gates 32, 36. While these gates 32, 36 are kept open by said gating signal, the up-down counter 34 and timer counter 37 continue counting. The pulse mixer 33 is intended to suppress the erroneous operation of the up-down counters 34 resulting from the abnormal simultaneous supply of output signals from the NAND gates 32, 36 to said counter 34 by offsetting said output signals. When counts made by the up-down counter 34 amount to a preset level, said counter 34 delivers a counted output to the program circuit 39 through NAND gates 40, 41 to prevent the NAND gates 32, 36 of the program circuit 39 from being supplied with any gating signal, thereby stopping the operation of the up-down counter 34 and timer counter 37. The NAND gate 40 is opened by being supplied with a calibration-instructing signal through an input terminal 42 only when measurement is made on a referential sample of fluid. Conversely where measurement is made on a test fluid whose particular chemical constituent is unknown, said NAND gate 40 remains closed to obstruct the passage of outputs from the up-down counter 34 and timer counter 37. The NAND gate 41 receives an output signal from a flip-flop circuit 43, and, when supplied with a reset output signal therefrom, allows the passage of a counted output signal from the NAND gate 40. When the flip-flop circuit 43 is set while not supplied with said counted output signal, then said circuit 43 delivers a set signal to the program circuit 39 in place of said counted output signal. When the NAND gate 36 is temporarily closed and the referential signal generator 35 ceases the supply referential pulses, then the timer counter 37 causes a register 44 to be stored with a complementary count to the capacity count of the timer counter 37. When measurement is made on a test fluid whose particular chemical constituent is unknown, the timer counter 37 is supplied with the complementary count stored in the register 44. The up-down counter 34 delivers its counted output in the digital form to the outside through an inverter 15.

Now let it be assumed that the referential signal generator 35 gives forth referential pulses at a frequency $f0$; the full count made by the up-down counter 34 amounts to $f0t1$; the up-down counter 34 delivers pulses having a number P1; and counting by the up-down counter 34 is previously brought to a state capable of making counts up to its capacity.

Where measurement is made on a referential sample of fluid under the above-mentioned conditions with the program circuit 39 supplied with a measurement-instructing signal through the input terminal 38, then the up-down counter commences up-down counting by being supplied with referential pulses from the referential signal generator 35 and, when supplied with an oscillation output from the voltage-frequency conversion oscillator 14, carries out up-counting. When the oscillation output is assumed to have a frequency $f2$, then the up-down counter 34 carries out down-counting of $f2-f0$ per unit time. Since $f2<f0$, counts stored in the up-down counter 34 gradually decrease from its capacity counts $fot1$. When the pulses counted by the up-down counter 34 reach the number P1, then a counted output signal from said counter 34 is conducted through the NAND gates 40, 41 to the program circuit 39 which in turn closes the NAND gates 32, 36. Now let it be assumed that the timer counter 37 continues counting for a time $nt1$. Then said time ntl is stored in the register 44. Namely, when the NAND gate 36 is closed, the register 44 is stored with a complementary number of pulses to those already counted by the timer counter 37 relative to the capacity of said timer counter 37. When the timer counter 37 again commences counting, it is stored with said complementary number of pulses from the register 44. Where, therefore, the timer counter 37 counts the same number of pulses as those previously counted, namely, where the timer counter 37 continues counting for a time $nt1$, that element of said timer counter 37 which is adjacent to the flip-flop circuit 43 supplies an overflow signal to said circuit 43 for setting. Then the NAND gate 41 supplies an output to the program circuit 39 to close the gates 32, 36 as previously described. As the result, the gates 32, 36 are left open for the aforesaid counting time ntl, thereby limiting the time for which the up-down counter 34 continues to count the number of pulses corresponding to analog signals derived from a fluid sample whose particular chemical constituent is unknown to the same length of time as the aforesaid counting time ntl. Since this counting time $nt1$ is stored in the register 44, the subsequent counting of pulses obtained from the unknown sample of fluid is also limited to said time $nt1$.

Even though a light-projected from the lamp 12a of FIG. 2 on, for example, the reagent carrier 11d may decrease in luminosity or drift current may appear in the photoelectric element 12e with the resultant change in the frequency of an oscillation output signal from the voltage-frequency conversion oscillator 14, yet the detecting system of this invention previously defines the time $nt1$ of counting continuously made by the timer counters 37 until the pulses counted thereby with respect to a referential sample of fluid reach the number P1, and determines the number of pulses used for measurement on the unknown sample of fluid and later counted by the up-down counter 34 for the above-mentioned time $nt1$. Namely, the detection system of this invention carries out determination by making compensation for the changed conditions such as the decreased luminosity of a light projected on a sample of fluid by means of automatic calibration, thereby attaining the accurate detection of the particular chemical constituent of a fluid. Further according to this invention, the arrangement of the calibration circuit is simplified, because said arrangement is based on a length of time for which the timer counter 37 continues to count pulses used in carrying out measurement on a referential sample of fluid. As mentioned above, therefore, even though a light projected from the lamp 12a on the respective reagent carriers may decline in luminosity or drift current may arise in the photoelectric element 12e, compensation can be effected by a simple circuit arrangement quickly with high precision for these changed conditions of measurement.

Figure 6:
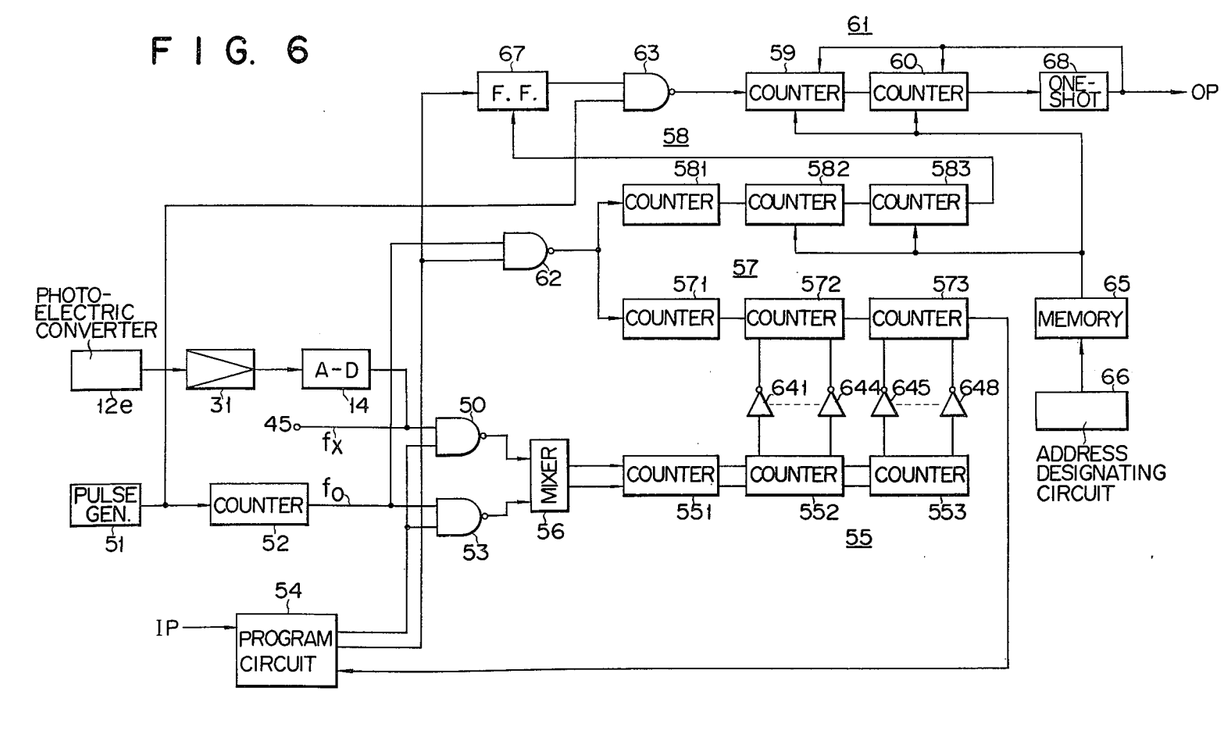
FIG. 6 is a block circuit diagram of the arithmetic operation circuit of FIG. 3.

Measured digital data which has been calibrated is subjected to arithmetic operation in the arithmetic operation circuit of FIG. 6. An output measured digital signal from the inverter of FIG. 5 thus calibrated is delivered to one input terminal of the NAND gate 50 of FIG. 6. Where no calibration is required, said output signal may be supplied directly from the A-D converter 14 to said NAND gate 50. Further, there is provided a clock pulse oscillator 51, whose output clock pulse is directly delivered to a 4-bit frequency conversion counter 52, which in turn generates a referential pulse $f0$ having a frequency equal to one-sixteenth of that of the clock pulse. This referential pulse $f0$ is supplied to one input terminal of a NAND gate 53. The other input terminals of the NAND gates 50, 53 are supplied with a gate control signal from a program circuit 54 to be opened for a prescribed length of time, during which an up-down counter 55 continues counting. Said up-down counter 55 consists of three 4-bit up-down counter elements 551, 552, 553 connected in series, namely, a 12-bit counter arrangement as a whole. An output $fx$ from the NAND gate 50 is supplied to the up-counting input terminal of said counter arrangement 55 through a pulse mixer 56. An output $f0$ from the NAND gate 53 is conducted to the down-counting input terminal of said counter arrangements 55 through said pulse mixer 56.

Further, there are provided first and second 12-bit arithmetic operation counters 57, 58 consisting of two groups of three series connected 4-bit counter elements at 571-572-573 and 581-582-583; and a third 8-bit arithmetic operation counter 61 consisting of two 4-bit counter elements 59, 60. A referential pulse $f0$ from the referential pulse generator 52 is supplied to the first and second arithmetic operation counters 57, 58 by passing through the series connected counter elements thereof. On the other hand, a clock pulse from the clock pulse generator 51 is delivered to the third arithmetic operation counter 61 through a fourth NAND gate 63 by passing through the series connected elements of said counter 61.

Parallel output signals from the up-down counter 55 are delivered in parallel to the respective elements of the first arithmetic operation counter 57 through the corresponding inverters 641, 642 ... 648 so as to supply said first arithmetic operation counter 57 with a complementary number of pulses to those $Px$ already counted. The second and third arithmetic operation counters 58, 61 are supplied from a memory device 65 with complementary numbers of pulses to the first and second counted operation data pulses PN.S corresponding to the kinds of the aforesaid counted pulses $Px$, namely, the kinds of various reagents measured by the photoelectric element 12e.

Those complementary numbers of pulses to the first and second counted operation data pulses PN.S which are delivered from memory device 65 in the forms corresponding to the kinds of measured reagents are read out from the addresses designated by an address-designating circuit 66 according to the kinds of measured reagents. The second and third arithmetic operation circuits 58, 61 are stored with said readout signals, before the third and fourth gates 62, 63 are opened to allow said arithmetic operation circuits 58, 61 to commence counting.

The program circuit 54 gives forth a different gate control signal from that which is used to control the first and second gates 50, 53. Said different gate control signal is supplied to the third gate 62 to open it in synchronization with the closing of said first and second gates 50, 53. At this time, the first arithmetic operation counter 57 is stored with a complementary number of pulses to those counted by the up-down counter 55, namely, the counted data pulses $Px$.

Outputs from the series connected elements 571, 572, 573 of the first arithmetic operation counter 57 are successively delivered to the program circuit 54 to convert the aforesaid gate signals into gate-closing signals, which in turn are supplied to the fourth gate 63 through a flip-flop circuit 67 to close said fourth gate 63 through the resetting of said flip-flop circuit 67.

Outputs from the series connected elements 581, 582, 583 of the second arithmetic operation counter 58 are successively transmitted to the fourth gate 63 through the flip-flop circuit 67 to open said fourth gate 63 through the setting of said flip-flop circuit 67.

An output signal from the series connected elements 59, 60 of the third arithmetic operation counter 61 which consists of a series of pulses is produced in the form of an arithmetic operation signal OP through a monostable multivibrator 68 and thereafter fed back to the third arithmetic operation counter 61 in the form of a presetting signal. Each time said arithmetic operation signal OP is generated, complementary numbers of pulses to the second operation data S corresponding to the respective measured reagents are read out as often as required from the memory device 65 as signals for presetting the distinguishing counter 74.

The program circuit 54 commences operation when supplied with a measurement-instructing signal IP introduced in synchronization with measurement by the photoelectric element 12e. When, under such condition, the photoelectric element 12e commences measurement, and the program circuit 54 receives a measurement-instructing signal IP, then the first and second gates 50, 53 are opened to deliver calibrated pulses $fx$ denoting the measured degrees of chemical reactions between a test fluid and the respective reagents from the terminal 45 to the up-counting input terminal of the up-down counter 55. At this time, referential pulses $f0$ from the referential pulse generator 52 are supplied to the down-counting input terminal of said up-down counter 55. Thus the up-down counter 55 simultaneously carries out the up-counting of said data pulses $fx$ and the down counting of referential pulses, causing the number of pulses introduced into said counter 55 to be repeatedly increased and decreased. If, in this case, both pulses $fx, f0$ are going to be simultaneously introduced, then the pulse mixer 56 will offset them, preventing the up-down counter 55 from being supplied with any more pulses.

Upon lapse of a preset time, the first and second gates 50, 53 are closed, bringing the counting of the up-down counter 55 to an end. At this time, determination is made of a difference between the number of pulses $fx$ counted for a preset time by the up-down counter 55 and that of referential pulses $f0$ counted during the same period, thereby providing data pulses $Px$ whose number is made to fall within a prescribed range regardless of the changed luminosity of measured reagent carriers by presetting a combination of various factors such as the frequency of referential pulses $f0$, the voltage-frequency conversion rate of the voltage control oscillator 14, the capacity of the up-down counter 55 and the time of counting. As soon as determination is made of the pulses $Px$ counted by the up-down counter 55, the first arithmetic operation counter 57 is supplied with a complementary number of pulses to said counted data pulses $Px$. At this time, the second and third arithmetic operation counters 58, 61 receive those complementary number of pulses to the first and second operation data pulses PN.S corresponding to the kinds of measured reagents which are read out from the addresses designated by the address-designating circuit 66 according to said measured reagents.

Under this condition, the third gate 62 is opened, and the first and second airthmetic operation counters 57, 58 are supplied with referential pulses $f0$ to commence the counting of said referential pulses $f0$. Since, at this time, the flip-flop circuit 67 is reset, and the fourth gate 63 is closed, the third arithmetic operation counter 61 is not actuated.

When the pulses counted by the second arithmetic counter 58 have the same number as the first data pulses PN, then said counter 58 gives forth an output to set the flip-flop circuit 67 and open the fourth gate 63. As the result, the third arithmetic operation counter 61 is supplied with clock pulses to commence counting, and generates an output operation signal OP, each time said counter 61 counts the second arithmetic operation signal S.

The first arithmetic operation counter 57 which has counted a P$x$ number of pulses produces an output to close the third gate 62 through the program circuit 54 and resets the flip-flop circuit 67 to close the fourth gate 63, thus bringing the action of all the arithmetic operation counters 57, 58, 61 to an end.

The first arithmetic operation counter 57 again commences counting to change the counted data pulses P$x$ with reference to referential pulses, and the second arithmetic operation counter 58 counts the first operation data pulses PN corresponding to the kinds of measured reagents. As the result, the third arithmetic operation counter 61 is supplied with a difference between the numbers of pulses counted by the first and second arithmetic operation counters 57, 58, namely, a difference between the number of counted data pulses P$x$ and the first operation data pulses PN, thereby carrying out a subtraction of P$x$-PN.

The third arithmetic operation counter 61 gives forth an arithmetic operation signal OP, each time said counter 61 counts the second operation data pulses S. Said arithmetic operation signal OP denotes the number of times the counting of the second operation data pulses S is repeated relative to a difference between the number of the counted data pulses P$x$ and that of the first operation data pulses PN, namely, a quotient arrived at by dividing said difference by the number of the second operation data pulses S, that is, carrying out a division of $(Px-PN)/S$.

In this case, the third arithmetic operation counter 61 supplied with clock pulses, actually counts pulses 16 times as many as pulses representing the aforesaid difference between the number of counted data pulses P$x$ and that of the first operation data pulses PN. To meet this situation, arithmetic operation is effected by multiplying the number of the second operation data pulses S similarly sixteen times in order to elevate the precision of arithmetic operation undertaken by the third arithmetic operation counter 61.

As mentioned above, the up-down counter 55 carries out up- and down-counting at the same time to determine the number of data pulses P$x$; a complementary number of pulses to said data pulses P$x$ are supplied to the first arithmetic operation counter 57 to be counted again with reference to referential pulses $f0$; simultaneously with said second time counting, the second and third arithmetic operation counters 58, 61 respectively carry out subtraction between the number of counted data pulses P$x$ and that of the first operation data pulses PN and division of said difference by the second operation data pulses S, namely, an arithmetic operation of $(Px-PN)/S$, thereby attaining an arithmetic operation using the counted data pulses P$x$ by a very simple arrangement.

Figure 7:
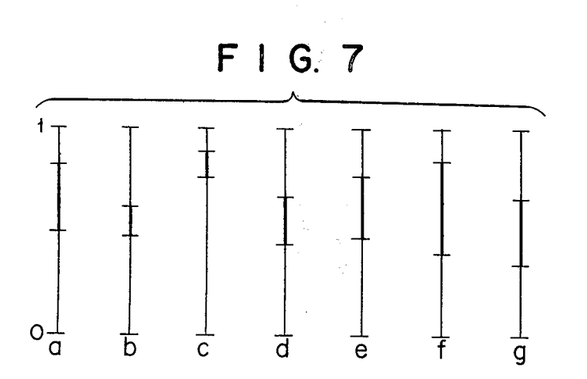
FIG. 7 is a schematic graphic representation of counted data obtained on various measured reagents.
Figure 8:
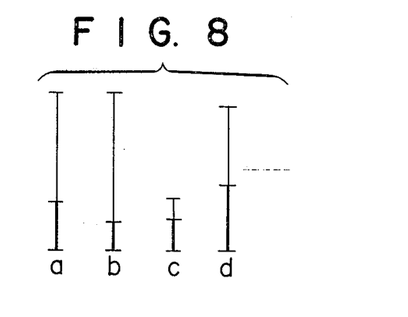
FIG. 8 is the graphic representation of counted data of FIG. 7.
Figure 9:
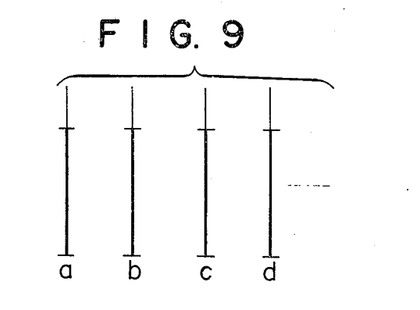
FIG. 9 is a graph showing the condition of counted data of FIG. 7 after completion of arithmetic operation.

Now let it be assumed that as shown in FIG. 7, the counted pulses P$xa$ to P$xg$ representing the various measured reagents $a$ to $g$ have numbers falling within the ranges denoted by the broad portions of the respective lines extending from the level of 1 to that of 0. Further, let it be assumed that the minimum numbers of these counted data pulses P$xa$ to P$xg$ are represented by PN$a$ to PN$g$, a coefficient by which the lengths of the above-mentioned broad portions or the ranges of the varying numbers of the pulses P$xa$ to P$xg$ can be equalized is designated as 1/S (where S is taken to have any optional value) and the aforesaid arithmetic operation is made of said counted data pulses P$xa$ to P$xg$ under such conditions. Then, the subtraction of P$x$-PN aligns the lower limits of the numbers of said counted data pulses P$xa$ to P$xg$ to a zero level as shown in FIG. 8, and the division of $(Px-PN)S$ brings the upper limits of the numbers of the pulses P$xa$ to P$xg$ to the same level as shown in FIG. 9. Namely, the numbers of the pulses P$xa$ to P$xg$ vary within the range between the zero level and the same upper level according to the kinds of the measured reagents $a$ to $g$. The above-mentioned process attains the very easy treatment of data pulses and elevates the precision of measurement thereof.

The data pulses which have been subjected to the above-mentioned arithmetic operation are supplied to one input terminal of the comparator 16. An output signal from the code detector 13 which denotes the type of a chemical reaction testing piece is supplied to the A-D conversion gate circuit 17 to be converted into a testing piece type-distinguishing digital signal which is transmitted as a readout-instructing signal to the memory device 18 which is previously stored with digital data signals obtained from a referential testing piece so as to define the sequential positions occupied by the degrees of chemical reactions between a test fluid and the reagents contained in the carriers constituting an actually measured testing piece 11. The testing piece type-distinguishing data cause the referential digital data pulses which correspond to the reagents of the carriers constituting an actually measured testing piece 11 to be successively read out from the memory device 18 according to the order in which the reagent carriers of said testing piece are measured, thereby determining the kinds of the reagents used.

Data on the degrees of referential chemical reactions successively read out from the memory device according to the above-mentioned testing piece-distinguishing data are delivered to the comparator 16 to be compared with data obtained on the degrees of reaction between a test fluid and the reagents of the carriers constituting an actually measured testing piece 11, thereby determining the sequential positions of the degrees of said chemical reactions. Data denoting said sequential positions are conducted to a printer 19 (FIG. 3) used as a final output device. This printer 19 is also supplied with testing piece type-distinguishing data delivered from the code detector 13 and prints out the results of measurement on a test report form 20 by selective operation of the printing mechanism by a combination of both types of data. If, in this case, a particular reagent carrier included in a given testing piece is intended for determination of the pH of, for example, urine, then selection is made from among the digit types (for example, 5, 6, 7, 8, 9) included in those of the printer 19 according to the testing piece type-distinguishing data and the digit type 5 is selected by data showing the degree of chemical reaction occurring in said particular reagent carrier to print out "pH5" on a test reporting form 20.

Figure 10:
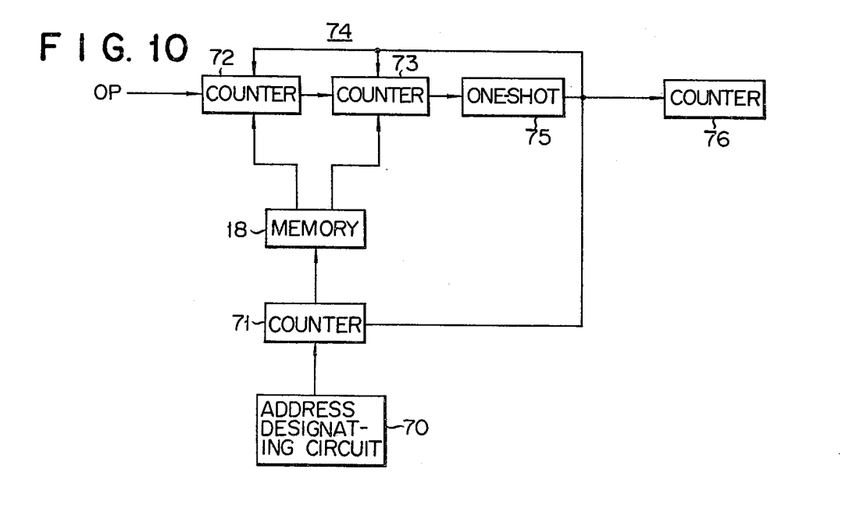
FIG. 10 is a concrete block circuit diagram of the comparator of FIG. 3.

The memory device 18 is successively stored with a plurality of groups of different numbers of pulses corresponding to the preset ranks, namely, a difference between the largest and the smallest numbers of pulses constituting each rank, starting with the lowest order rank. A readout address-designating circuit 70 causes a counter 71 for designating the readout address of the memory device 18 to be supplied with a signal denoting the address bearing the data (or a difference between the largest and the smallest numbers of pulses) of the lowest order rank. A complementary number of pulses to the rank data stored in said address is read out from the memory device 18 and supplied to the testing piece type-distinguishing counter 74 consisting of two series connected 4-bit counter elements 72, 73. Said distinguishing counter 74 counts the number of introduced pulses constituting the arithmetic operation output OP used as measurement data. An output signal from the distinguishing counter 74 consisting of a series of bits is conducted through the monostable multivibrator 75 to the rank recording counter 76 and the readout address designating counter 71 so as to be counted thereby. Thereafter, the distinguishing counter 74 is supplied with the rank data stored in the immediately succeeding address designated by the readout address-designating circuit 70.

When, under the above-mentioned arrangement, the readout address designating circuit 70 is operated, then the readout address-designating counter 71 is supplied with a signal denoting the address bearing the data of the lowest order rank, and the distinguishing counter 74 receives that complementary number of counts to the rank data which is stored in said address and read out from the memory device 18.

Where, under the above-mentioned condition, the distinguishing counter 74 is supplied with an arithmetic operation output OP, the pulses constituting said output OP begin to be counted, and the distinguishing counter 74 counts an equal number of pulses to those representing the data of the lowest order rank, then the distinguishing counter 74 produces a rank signal, which in turn is delivered to the readout address-designating counter 71 to increase the number of pulses previously counted thereby by one, causing the distinguishing counter 74 to be supplied with the immediately following rank data. Since, at this time, the address designated by the readout address-designating counter 71 is shifted up by one address, the memory device 18 delivers data denoting a rank occupying an immediately higher position and supplies said data to the distinguishing counter 74.

Where the distinguishing counter 74 continues to count the number of pulses constituting the measurement data OP until an equal number of pulses to those denoting the lowest order rank are counted, then said distinguishing counter 74 generates the succeeding rank signal. This operation is repeated thereafter.

Each time the distinguishing counter 74 previously supplied with a complementary number of pulses to the rank data pulses counts an equal number of pulses to said rank data pulses, then said counter 74 produces the following rank signal to shift upward the address designated by the address-designating counter 71 by one address and is successively supplied with a complementary number of pulses to those constituting each rank of higher order.

Accordingly, each time the upper limit of the number of pulses constituting each rank is exceeded by the number of pulses of measurement data OP counted by the distinguishing counter 74, the succeeding rank signal is given forth by said counter 74. Therefore, the rank represented by the pulses of the measurement data OP can be determined from the pulses supplied to the rank recording counter 76. For example, where no pulse is supplied to the recording counter 76, then it means that the number of pulses denoting the measurement data OP is smaller than that of the lowest order rank, namely, that the pulses of the measurement data OP represent the lowest order rank. Where only one pulse is counted by the rank recording counter 71, then it shows that the count of the measurement data OP represents a rank immediately higher than the lowest order rank.

As mentioned above, the detecting system of this invention has a very simple arrangement comprising a memory device 18; a readout address-designating circuit 70 for designating the readout address of the memory device 18; a readout address-designating counter 71 for shifting the position of a readout address upward successively by one address, each time a rank signal is supplied to said counter 71; a distinguishing counter 74 for counting the pulses of the measurement data when supplied from the memory device 18 with a complementary number of pulses to that of rank data; a monostable multivibrator 75 for converting an output rank signal from the distinguishing counter 74 into pulses; and a rank recording counter 76 for counting pulses constituting said rank signal, thereby carrying out an easy operation consisting of the steps of successively supplying the memory device 18 with rank data represented by a difference between the largest and smallest numbers of pulses constituting each rank, starting with the lowest order rank; designating the address bearing the data of the lowest rank by a readout address-designating circuit 70; counting the pulses constituting the measurement data by the distinguishing counter 74; finding the number of pulses counted by the rank recording counter; and determining the rank denoted by the measurement data OP according to the number of pulses constituting said data OP.

Further, when the memory device 18 is stored with rank data associated with various kinds of measured reagents and the readout address designated by the readout address-designating circuit 70 is changed according to the kinds of said measured reagents, then it will be possible to determine the ranks represented by the various kinds of measured reagents.

Figure 11:
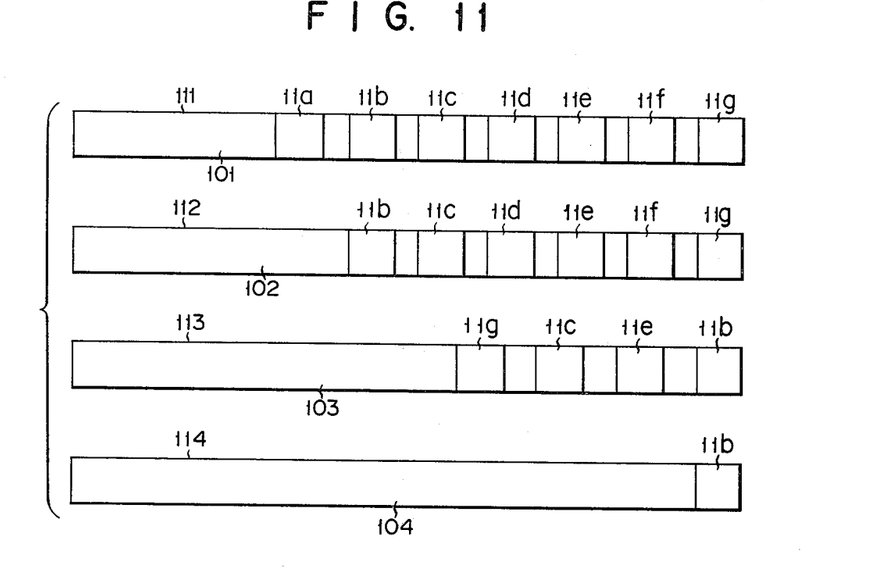
FIG. 11 is a plan view of one form of the chemical reaction testing pieces used in this invention.

According to the embodiment of FIG. 3, the code detector 13 detected the kinds of reagents mounted on the chemical reaction testing piece 11 and the sequential positions of the reagent carriers arranged on said testing piece 11. Referential data were read out from the memory device 18 and the types of the printer 19 were selected according to data on the kinds of reagents and the sequential positions of reagent carriers. However, a chemical reaction-testing piece used in such test is not limited to the form used in this embodiment. As shown in FIG. 11, however, there are many other forms of testing pieces such as the testing pieces 111, 112, 113, 114, of which the testing piece 111 bears numerous reagent carriers 11a to 11g mounted on the transparent substrate 101, and of which the testing piece 114 has a single carrier 11b disposed on the transparent substrate 104. Further, there are used, though not shown, still other forms of testing pieces, such as those which have the same number of reagent carriers containing different kinds of reagents and arranged in different patterns or fitted at different points. Therefore, the forms of chemical reaction-testing pieces have to be distinguished before determination is made of the degrees of chemical reactions between a test fluid and the reagents contained in the carriers, giving rise to the problem of rendering an automatic detection system complicated.

Figure 12:
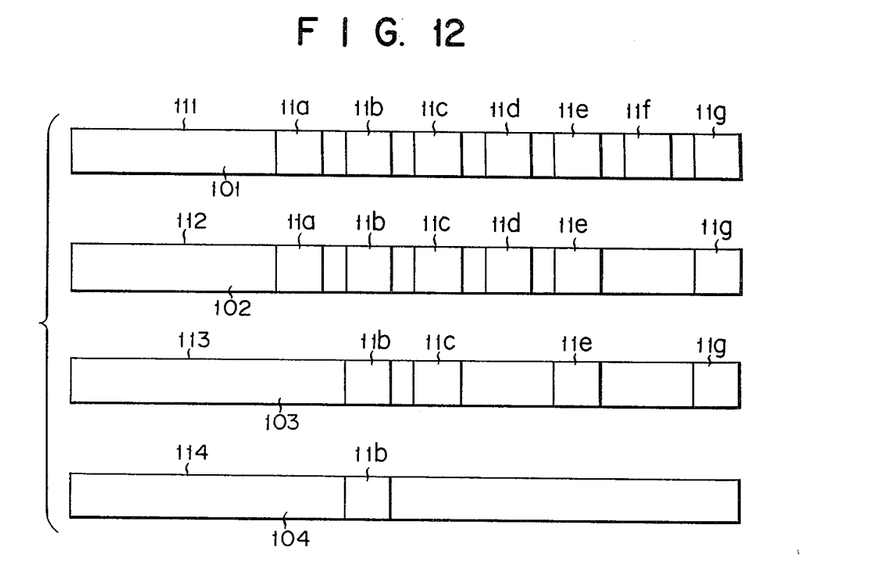
FIG. 12 is a plan view of another form of the chemical reaction testing pieces used in the invention.

The testing piece of FIG. 12 has the form developed to eliminate the above-mentioned difficulties. Namely, according to this form, one or more reagent carriers are arranged on a substrate in the order and at the points specified for the reagents used, enabling the degrees of chemical reactions between a test fluid and the reagents contained in the carriers thus arranged to be successively determined in the specified order. In FIG. 12. the carriers 11a to 11g bearing different reagents are arranged on narrow transparent substrates 101 to 104 in the order and at the points specified for said different reagents. In this case, the reagent carriers 11a to 11g are not always disposed on all the substrates 101 to 104. Namely, the testing piece 112 is provided with the reagent carriers 11a to 11e and 11g, the testing piece 113 with the reagent carriers 11b, 11c, 11e and 11g, and the testing piece 114 with the reagent carrier 11b alone, said carriers being provided on the substrate in the order and at the points specified for the reagents contained therein. Therefore, the chemical reaction-testing pieces 111 to 114 of FIG. 12 can be regarded to have the same form, admitting of automatic detection, without the necessity of previously distinguishing the form of the testing pieces. The reason is that where any of such testing pieces as shown in FIG. 12 is set in a prescribed position in an automatic detecting device, then the reagent carriers are located at the points specified for the reagents contained therein, and that where any of said testing pieces is not provided with a carrier corresponding to any specified point, then it will be sufficient to confirm the absence of a carrier at said point. The fact that the testing pieces of FIG. 12 can be regarded to have the same form enables determination to be carried out in a uniform length of time, thereby elevating the precision of said determination.

As mentioned above, the automatic detection system of this invention draws upon the facts that the rate at which light reflects from a given reagent carrier varies with the degree of a chemical reaction occurring between a test fluid and the reagent contained in said carrier and that the number of pulses constituting measurement data obtained from a photoelectric element linearly varies with the degree of said chemical reaction, and is further characterized in that the sequential position of the degree of a given chemical reaction is determined electrically or automatically by comparing data on the measured degree of a chemical reaction with data on the prescribed referential chemical reaction. Accordingly, the automatic detection system of this invention carries out measurement on a chemical reaction-testing piece without giving rise to errors resulting from the mental differences of individuals engaged in measurement, as is the case with the prior art process based on the naked eye collation of measured degrees of chemical reactions occurring in the respective reagent carriers provided on a testing piece with a colorimetric chart.

What is claimed is:

1. A system for detecting the particular chemical constituent of a fluid which comprises a chemical reaction-testing piece including a plurality of absorption reagent carriers arranged on a narrow transparent substrate at a prescribed interval, such that the kinds of the respective reagents and the positions of their carriers on the substrate can be indicated by coded signals representing said arrangement and the positions of the exposed transparent portions of the substrate intervening between said reagent carriers; a memory device for storing data corresponding to reference chemical reactions used to determine the sequential positions of the degrees of cheimcal reactions between a test fluid and the reagents contained in the plural absorptive carriers mounted on the chemical reaction-testing piece; a first photoelectric conversion element for successively scanning the exposed transparent portions of the substrate of the chemical reaction-testing piece and the reagent carriers spatially arranged on the substrate to provide a coded signal distinguishing the type of said testing piece; a code detector coupled to said first photoelectric conversion element for obtaining from an output signal from said first photoelectric conversion element the data which distinguishes the type of the testing piece and the positions of the reagent carriers disposed on the substrate of said testing piece; a second photoelectric conversion element for providing electric signals denoting those optical changes occurring in the respective reagent carriers mounted on the substrate of the testing piece which correspond to the degrees of the chemical reactions between a test fluid and the reagents contained in said carriers; an analog-digital converter for converting said electric signals into digital signals denoting the measured degrees of chemical reactions; an arithmetic operation device for providing data on the measured degrees of chemical reactions from digital output signals from said analog-digital converter; a gate circuit for reading out from the memory device the data on the reference chemical reactions which correspond to the measured reagents by using said testing piece type-distinguishing data; a comparator for comparing the readout data on the reference chemical reactions with the data on the measured degrees of chemical reactions in the tested reagent carriers to determine the sequential positions of said measured degrees of chemical reactions; and a printing device for printing out the results of said determination on a recording sheet of paper according to the data on the sequential positions of the measured degrees of chemical reactions and the testing piece type-distinguishing data.

2. A detection system according to claim 1, wherein said analog-digital converter comprises a voltage controlled oscillator for generating a signal whose frequency denoting measured data varies with the level of said electric signal; and means for supplying the voltage controlled oscillator with an analog signal derived from a reflector of prescribed reflectivity so as to provide a signal having a reference frequency; and said arithmetic operation device comprises means for counting output pulses from said voltage controlled oscillator; means for storing a signal corresponding to a length of time required to count a prescribed number of pulses constituting said signal of reference frequency; means coupled to said counting means and storing means for causing said counting means to count the pulses of said signal of reference frequency for the stored length of time; and a calibration device for calibrating the number of pulses constituting the signal whose frequency denotes measured data by the number of pulses constituting the signal of reference frequency.

3. A detection system according to claim 1, wherein the arithmetic operation device comprises a clock pulse generator; an up-down counter whose up-counting terminal is supplied with an output signal from the analog-digital converter and whose down-counting terminal is supplied with an output signal from said pulse generator; an arithmetic operation counter; means for supplying the arithmetic operation counter with those complementary numbers of pulses to the pulses already counted which are still stored in the up-down counter; and means for causing the arithmetic operation counter to count said clock pulses and at the same time carry out arithmetic operations.

4. A detection system according to claim 1, wherein the comparator comprises a distinguishing counter supplied with those complementary numbers of pulses to data on reference chemical reactions which were previously stored in the memory device; means for causing the distinguishing counter thus supplied to count pulses constituting data on the measured degrees of chemical reactions; means for coupling out a rank signal from the distinguishing counter, each time the number of pulses constituting data on the measured degree of a chemical reaction which is counted by the distinguishing counter coincides with that of pulses constituting rank data; a rank recording counter for counting the pulses of said rank signal; means for supplying the distinguishing counter with pulses representing a rank of immediately higher order than the rank whose sequential position was previously determined; and means for distinguishing the ranks of data on the measured degrees of chemical reactions from the number of pulses supplied to the rank recording counter.

5. A detection system according to claim 1, wherein the chemical reaction-testing piece comprises of one or more absorptive reagent carriers arranged on a narrow transparent substrate at a prescribed interval in the order and at the points specified for the kinds of the reagents contained in said absorptive reagent carriers.

* * * * *